United States Patent [19]
Kristen L. Manion et al.

[11] Patent Number: 5,132,087
[45] Date of Patent: Jul. 21, 1992

[54] APPARATUS FOR MEASURING BLOOD CONSTITUENT COUNTS

[76] Inventors: Kristen L. Manion, 2600 San Leandro Blvd., Apt. 1508, San Leandro, Calif. 94578; Stephen C. Wardlaw, 191 N. Cove Rd., Old Saybrook, Conn. 06475; Robert A. Levine, 31 Pilgrim La., Guilford, Conn. 06437

[21] Appl. No.: 421,639

[22] Filed: Oct. 16, 1989

[51] Int. Cl.$^5$ .............................................. G01N 15/05
[52] U.S. Cl. ..................................... 422/58; 73/61.63; 356/39; 422/61; 422/99; 422/104; 436/70
[58] Field of Search .................... 436/70, 808, 810; 422/61; 73/61.4, 61.1 R, 865.9; 356/39; 350/526; 210/744

[56] References Cited

U.S. PATENT DOCUMENTS

| | | | |
|---|---|---|---|
| 4,137,755 | 2/1979 | Wardlaw et al. | 73/61.1 R |
| 4,156,570 | 5/1979 | Wardlaw | 73/747.61 |
| 4,181,609 | 1/1980 | Wardlaw et al. | 210/774 |
| 4,774,965 | 10/1988 | Rodriguez et al. | 73/61.1 R |
| 4,875,364 | 10/1989 | Levine et al. | 436/70 |
| 4,887,458 | 12/1989 | Baker et al. | 436/70 |
| 4,953,975 | 9/1990 | Levine et al. | 73/61.1 R |

OTHER PUBLICATIONS

Fisher Scientific Instrumentation Laboratory Catalog 1988 pp. 207, 229 and 1418.

*Primary Examiner*—Robert J. Hill, Jr.
*Attorney, Agent, or Firm*—William W. Jones

[57] ABSTRACT

Blood constituents are separated by centrifugation in a transparent tube which contains a float for physically elongating certain of the constituents. The centrifuged sample in the tube is positioned on a layer measuring device with which red cell and buffy coat constituent band heights can be measured in ambient light. The buffy coat constituent measurements are made under optical magnification. The measuring device has a mathematically derived red cell layer nomogram printed thereon, and a separate scale for measuring buffy coat constituent bands. Conversion tables are provided for converting the measured buffy coat constituent band lengths into constituent cell counts. The measuring device includes tube-engaging portions for properly positioning the tube during the measurements, and the red cell scale automatically compensates for the presence of the float and densification of red cells needed for proper banding.

2 Claims, 7 Drawing Sheets

| Plts Lymphs & Monos Grans | Volume conversion factor | | | | | |
|---|---|---|---|---|---|---|
| | 100 | 120 | 160 | 200 | 240 | 280 |
| 0.2 | 25 / 0.9 / 0.8 | 30 / 1.1 / 0.9 | 40 / 1.5 / 1.2 | 50 / 1.8 / 1.5 | 60 / 2.2 / 1.9 | 70 / 2.5 / 2.2 |
| 0.4 | 50 / 1.8 / 1.5 | 60 / 2.2 / 1.9 | 80 / 2.9 / 2.5 | 100 / 3.6 / 3.1 | 120 / 4.3 / 3.7 | 140 / 5.1 / 4.3 |
| 0.6 | 75 / 2.7 / 2.3 | 90 / 3.3 / 2.8 | 120 / 4.4 / 3.7 | 150 / 5.4 / 4.6 | 180 / 6.5 / 5.5 | 210 / 7.6 / 6.3 |
| 0.8 | 100 / 3.6 / 3.1 | 120 / 4.3 / 3.7 | 160 / 5.8 / 4.9 | 200 / 7.2 / 6.2 | 240 / 8.7 / 7.4 | 280 / 10 / 8.6 |
| 1.0 | 125 / 4.5 / 3.9 | 150 / 5.4 / 4.6 | 200 / 7.3 / 6.2 | 250 / 9.1 / 7.7 | 300 / 11 / 9.2 | 350 / 13 / 11 |
| 1.2 | 150 / 5.4 / 4.6 | 180 / 6.5 / 5.5 | 240 / 8.7 / 7.4 | 300 / 11 / 9.2 | 360 / 13 / 11 | 420 / 15 / 13 |
| 1.4 | 175 / 8.0 / 5.4 | 210 / 9.6 / 6.5 | 280 / 13 / 8.6 | 350 / 16 / 11 | 420 / 19 / 13 | 490 / 22 / 15 |
| 1.6 | 200 / 9.1 / 6.2 | 240 / 11 / 7.4 | 320 / 15 / 9.9 | 400 / 18 / 12 | 480 / 22 / 15 | 560 / 26 / 17 |
| 1.8 | 225 / 10 / 6.9 | 270 / 12 / 8.3 | 360 / 16 / 11 | 450 / 21 / 14 | 540 / 25 / 17 | 630 / 29 / 19 |
| 2.0 | 250 / 11 / 7.7 | 300 / 14 / 9.2 | 400 / 18 / 12 | 500 / 23 / 15 | 600 / 27 / 19 | 700 / 32 / 22 |
| 2.2 | 275 / 13 / 8.5 | 330 / 15 / 10 | 440 / 20 / 14 | 550 / 25 / 17 | 660 / 30 / 20 | 770 / 35 / 24 |
| 2.4 | 300 / 14 / 9.2 | 360 / 16 / 11 | 480 / 22 / 15 | 600 / 27 / 18 | 720 / 33 / 22 | 840 / 38 / 26 |
| 2.6 | 325 / 15 / 10 | 390 / 18 / 12 | 520 / 24 / 16 | 650 / 30 / 20 | 780 / 36 / 24 | 910 / 42 / 28 |
| 2.8 | 350 / 16 / 11 | 420 / 19 / 13 | 560 / 26 / 17 | 700 / 32 / 22 | 840 / 38 / 26 | 980 / 45 / 30 |
| 3.0 | 375 / 17 / 12 | 450 / 21 / 14 | 600 / 27 / 18 | 750 / 34 / 23 | 900 / 41 / 28 | >999 / 48 / 32 |
| 3.2 | 400 / 18 / 12 | 480 / 22 / 15 | 640 / 29 / 20 | 800 / 37 / 25 | 960 / 44 / 30 | >999 / 51 / 35 |
| 3.4 | 425 / 19 / 13 | 510 / 23 / 16 | 680 / 31 / 21 | 850 / 39 / 26 | >999 / 47 / 31 | >999 / 54 / 37 |
| 3.6 | 450 / 21 / 14 | 540 / 25 / 17 | 720 / 33 / 22 | 900 / 41 / 28 | >999 / 49 / 33 | >999 / 58 / 39 |
| 3.8 | 475 / 22 / 15 | 570 / 26 / 18 | 760 / 35 / 23 | 950 / 43 / 29 | >999 / 52 / 35 | >999 / 61 / 41 |
| 4.0 | 500 / 23 / 15 | 600 / 27 / 18 | 800 / 37 / 25 | >999 / 46 / 31 | >999 / 55 / 37 | >999 / 64 / 43 |
| 4.2 | 525 / 24 / 16 | 630 / 29 / 19 | 840 / 38 / 26 | >999 / 48 / 32 | >999 / 58 / 39 | >999 / 67 / 45 |
| 4.4 | 550 / 25 / 17 | 660 / 30 / 20 | 880 / 40 / 27 | >999 / 50 / 34 | >999 / 60 / 41 | >999 / 70 / 47 |
| 4.6 | 575 / 26 / 18 | 690 / 32 / 21 | 920 / 42 / 28 | >999 / 53 / 35 | >999 / 63 / 43 | >999 / 74 / 50 |
| 4.8 | 600 / 27 / 19 | 720 / 33 / 22 | 960 / 44 / 30 | >999 / 55 / 37 | >999 / 66 / 44 | >999 / 77 / 52 |
| 5.0 | 625 / 29 / 19 | 750 / 34 / 23 | >999 / 46 / 31 | >999 / 57 / 39 | >999 / 69 / 46 | >999 / 80 / 54 |

Height of component layer (in mm.)

FIG-8

APPARATUS FOR MEASURING BLOOD CONSTITUENT COUNTS

FIELD OF THE INVENTION

This invention relates to the measurement of blood constituent counts from a sample of centrifuged blood in a transparent tube, and more particularly, relates to a device for making such measurements under ambient light conditions.

RELATED ART

A technique and paraphenalia have been developed for measuring blood constituent counts from a sample of whole blood which has been centrifuged in a transparent tube which contains a blood constituent-highlighting stain and an elongated float which floats on the red cell layer and elongates the buffy coat constituent layers after centrifugation. The aforesaid technique is disclosed generally in U.S. Pat. Nos. 4,027,660 Wardlaw et al; 4,082,085 Wardlaw et al; and 4,137,755 Wardlaw et al. The technique also benefits from the use of potassium oxalate as an anticoagulent and red cell densifyer, as described in U.S. Pat. No. 4,181,609 Wardlaw et al. The cell counts are obtained by measuring the cell band lengths in specialized instruments which use onboard microprocessors for converting band lengths to cell counts. Such instruments are disclosed in U.S. Pat. Nos. 4,156,570 Wardlaw; 4,209,226 Wardlaw et al; and 4,558,947 Wardlaw. A manually operable instruments which does not require an onboard microprocessor, but which uses specially calibrated cards is also proposed in U.S. Pat. No. 4,259,012 Wardlaw. This instrument, as do the previously referenced reading instruments, utilizes an electrical light illumination source for enhanced fluorescence of the stain used in the centrifuge tube. The tube and float paraphenalia have also found utility in the detection of blood-borne parasites, as described in U.S. Pat. No. 4,190,328 Levine et al.

It is highly desirable that the aforesaid technique and paraphenalia be usable in the field, as contrasted to in a laboratory, so that on the spot field diagnosis of at least potential problems would be rendered possible. This is particularly true in the investigation of blood borne parasite infestations, such as malaria, which are prevalent in more primitive environs where electricity may not be available, or where laboratory facilities suitable for the aforesaid instrumentation are not handy. In connection with such field diagnosis of malaria, it has been determined that medical personnel engaged in such malaria diagnosis will benefit from the ability to measure both hematocrit and the platelet count in a patient's blood, as well as being able to determine the presence or absence of the malarial parasites in the blood sample.

SUMMARY OF THE INVENTION

One embodiment of this invention relates to a compact pocket size device which can be used to measure hematocrit and platelet counts in the field using ambient light to discern the band interfaces in question. The device can derive the aforesaid blood constituent information from a centrifuged blood sample contained in a capillary or other transparent tube. A specialized form of a nomogram is displayed on one side of the device, along with means for properly positioning the tube in overlay fashion on the nomogram. The nomogram is adapted to take into account the presence of the float in the tube, and the red cell densification occasioned by the potassium oxalate in the blood sample, whereby the information obtained from properly aligning the tube on the nomogram can be used to determine the sought blood constituent values, i.e. the hematocrit reading, and the platelet count. A scale is also disposed on the device for measuring the platelet band length. Optical magnification of the platelet band scale and the adjacent tube is preferably provided by means of a magnifying lens integrally mounted on the device. The device itself preferably takes the form of a plaque which may be formed from a plastic material such as acrylic or the like. The nomogram-platelet scale, or the reading side, of the plaque is suitably contoured so that a reference stop surface will be provided for bearing against the closed end of the centrifuge tube, and the tube will remain in proper position relative to the nomogram reference lines, and to the platelet scale. The magnifying lens may be set in an integral frame formed on the plaque adjacent to the platelet scale. Numerical indicia will also be printed on the reading side of the plaque. On the opposite side of the plaque are printed conversion tables for translating the readings into platelet counts. The hematocrit will be read directly off of the nomogram. The device can also be used to determine white cell counts with an appropriate conversion table.

It is therefore an object of this invention to provide a device which enables quick readings of hematocrit and buffy coat constituent counts to be made using ambient light conditions.

It is a further object of this invention to provide a device of the character described which includes a special nomogram which is designed to perform hematocrit readings from a centrifuged blood sample disposed in a transparent tube containing a constituent-elongating float.

It is an additional object of this invention to provide a device of the character described wherein the tube is placed on the device over the nomogram to perform the hematocrit reading.

It is another object of this invention to provide a device of the character described which is small enough to be carried in one's pocket, and is especially useful in field investigations.

These and other objects and advantages of this invention will become more readily apparent from the following detailed description of a preferred embodiment thereof when taken in conjunction with the accompanying drawings, in which:

BRIEF DESCRIPTION OF THE DRAWINGS

FIG. 8 is a plan view of the reverse side of the device of FIG. 7.

DETAILED DESCRIPTION OF THE INVENTION

Figure 1:
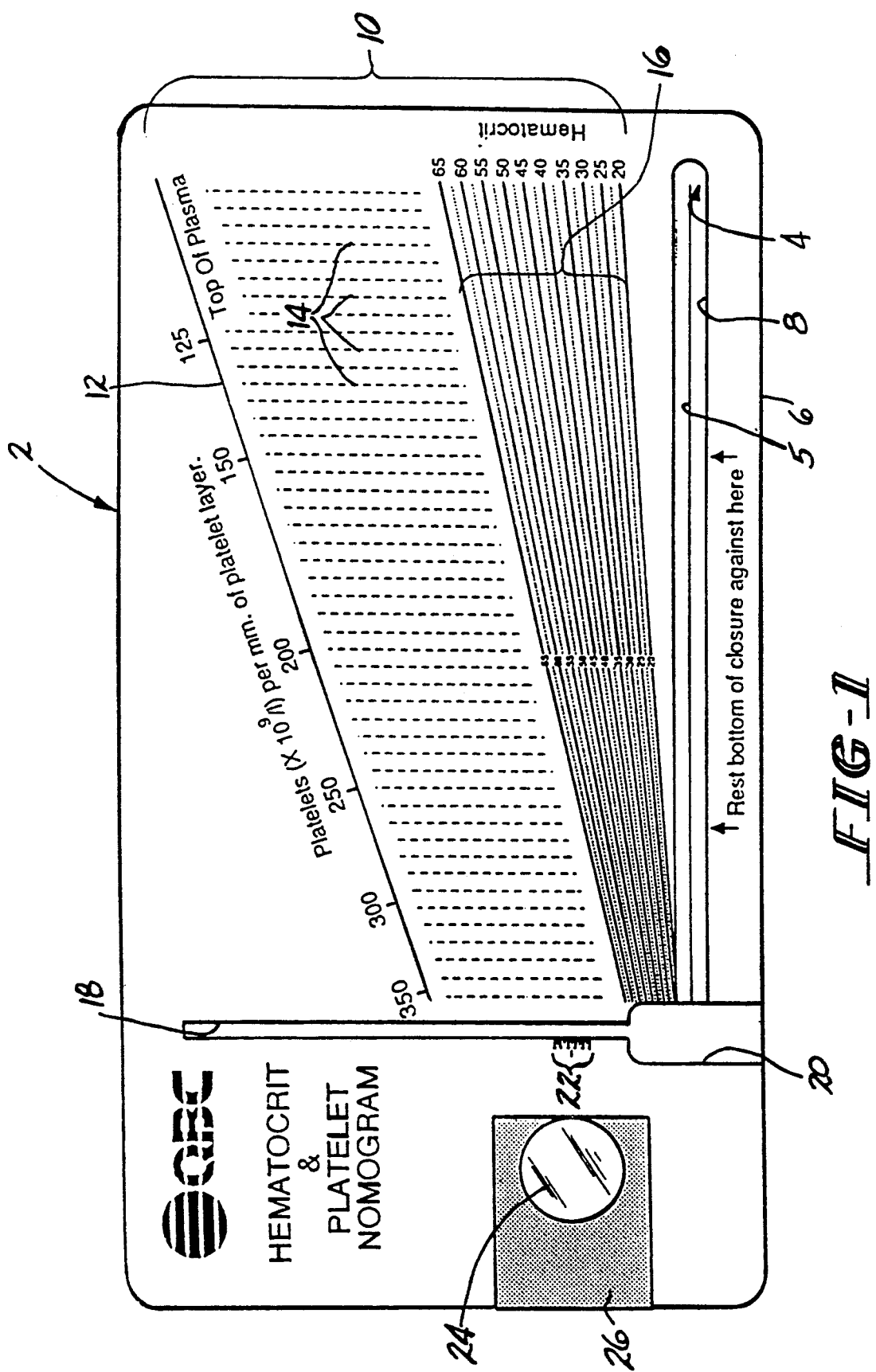
FIG. 1 is a plan view of the nomogram or reading surface of a preferred embodiment of this invention.

Referring now to FIG. 1, a preferred embodiment of the device denoted generally by the numeral 2 is shown. The device 2 preferably takes the form of a generally rectangular plaque and can be readily held in one hand, and is sized to fit in one's pocket. The device 2 is thus compact and particularly suitable for use in the field by medical personnel. A groove 4 is formed adjacent to the bottom edge 6 of the device 2, the groove 4 forming a reference stop surface 8 against which the bottom of the centrifuge tube is positioned when making the total volume and hematocrit readings. When a clay plug or an integral closure wall is used to close the bottom of the tube rather than a plastic plug, a reference line 5 is provided in the groove 4 for alignment with the bottom of the tube. The nomogram 10 is printed on the device 2 above the groove 4. The uppermost line 12 in the nomogram 10 is a reference line for alignment with the top of the plasma layer in the centrifuge tube. Platelet packing values are printed on the device 2 in conjunction with the fill reference line 12. Elongated recesses or corrugations 14 are formed in the device 2 extending between the groove 4 and the fill reference line 12 for the purpose of ensuring that the tube stays perpendicular to the stop surface 8 when the readings are taken. The lower portion 16 of the nomogram 10 constitutes hematocrit reference lines which have associated numerical indicia from which the hematocrit reading can be derived. A slot 18 for receiving the centrifuge tube while measuring the buffy coat constituent band length is formed on one side of the device 2. An enlarged notch 20 is associated with the slot 18 for reception of a basal tube closure plug when one is used with the centrifuge tube. A scale 22 is printed on the device 2 adjacent to the slot 18 whereby the length of the constituent band can be accurately measured, preferably in millimeters. A magnifying lens 24 mounted in a holder 26 is aligned with the scale 22 to facilitate use of the latter. The lens 24 is preferably a 10× lens.

Figure 2:
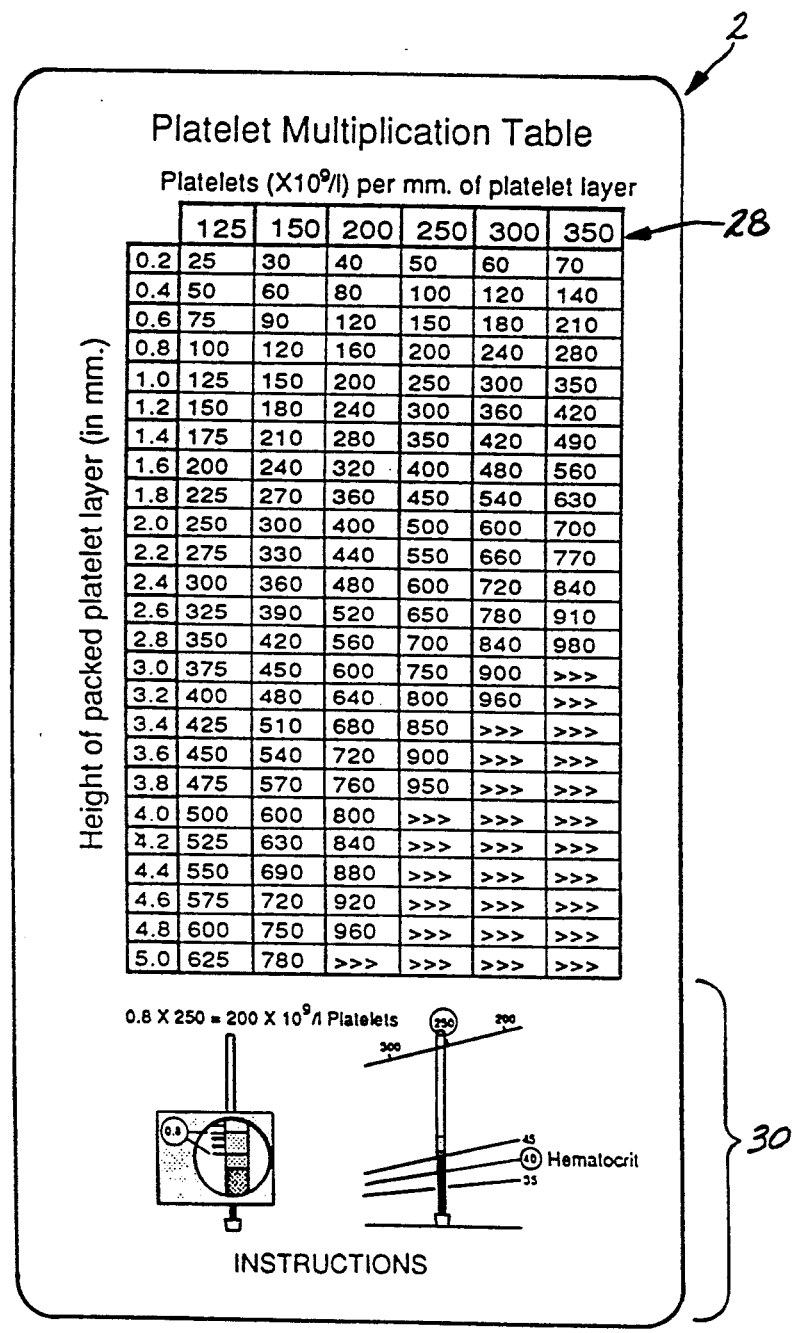
FIG. 2 is a plan view of the reverse side of the device of FIG. 1.

FIG. 2 shows the reverse side of the device 2 on which a conversion table is printed which is used to convert the measured buffy coat constituent band length into a count. The specific table shown is one which is used to obtain a platelet count from the length of the platelet band in the buffy coat. The reference numbers 28 are the numbers taken from the total fill reference line 12 on the front of the device 2. Use instructions are printed on the lower portion 30 of the back of the device 2.

Figure 3:
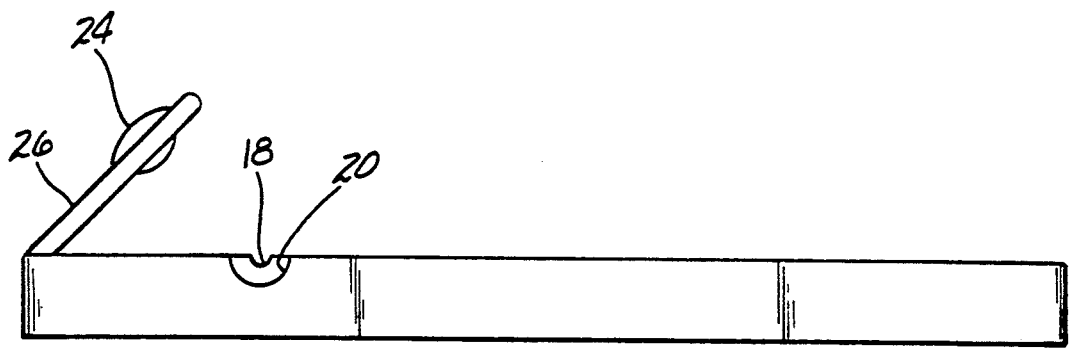
FIG. 3 is an elevational view of the device as viewed from the bottom of FIG. 1.

FIG. 3 illustrates the thickness of the plaque, and the positioning of the lens 24 and lens holder 26 with respect to the slot 18 and the notch 20.

Figure 6:
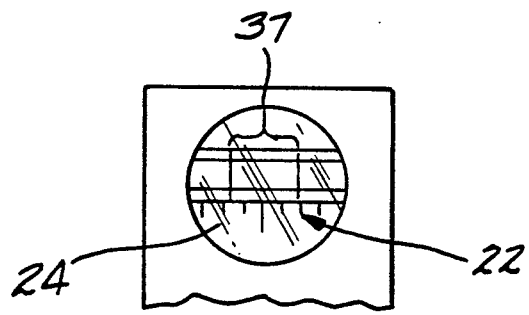
FIG. 6 is a view of the magnified scale and constituent band one sees when measuring the length of the constituent band.
Figure 4:
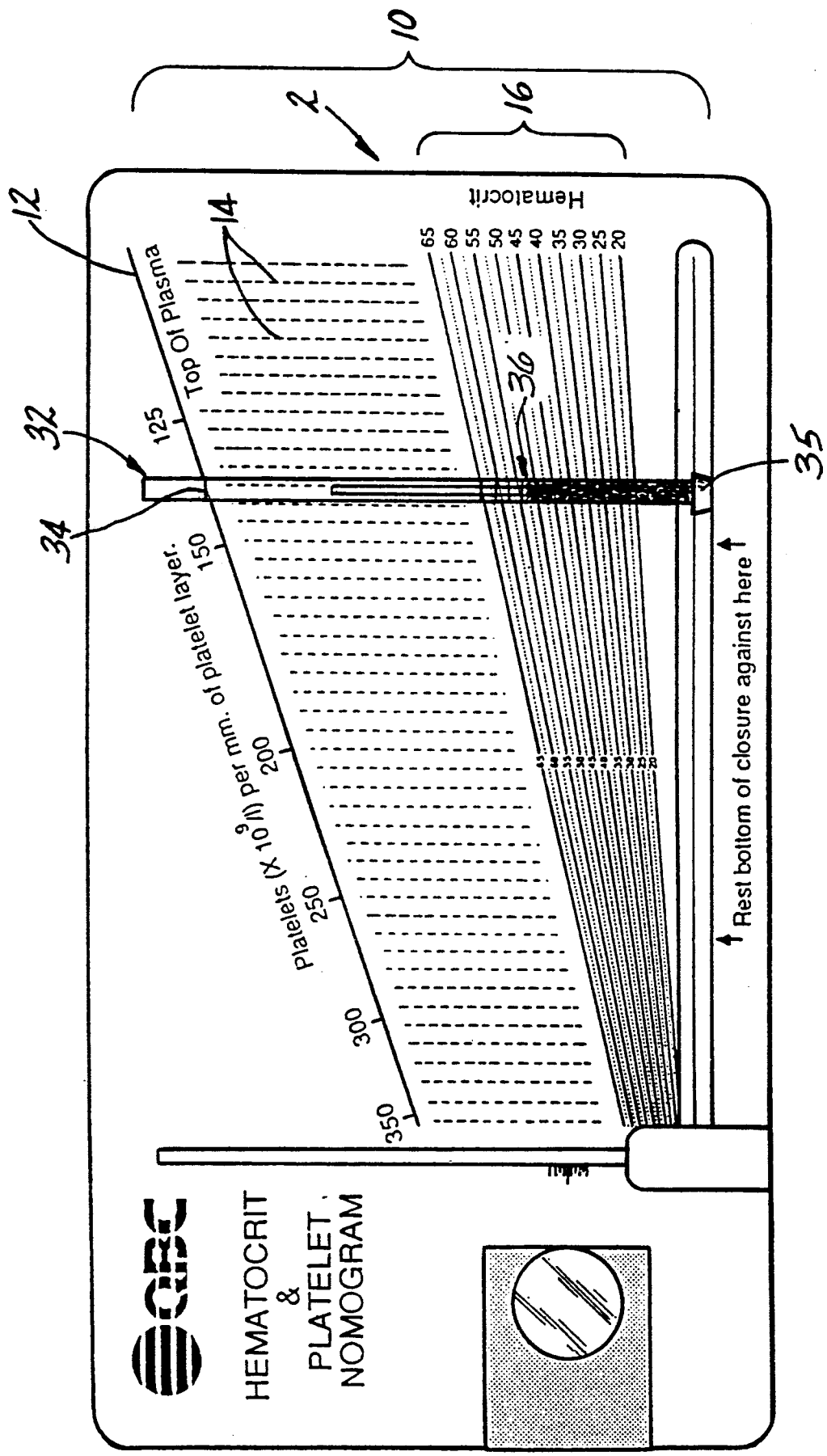
FIG. 4 is a view similar to FIG. 1 but showing a centrifuge tube with a blood sample in position on the nomogram for reading hematocrit.
Figure 5:
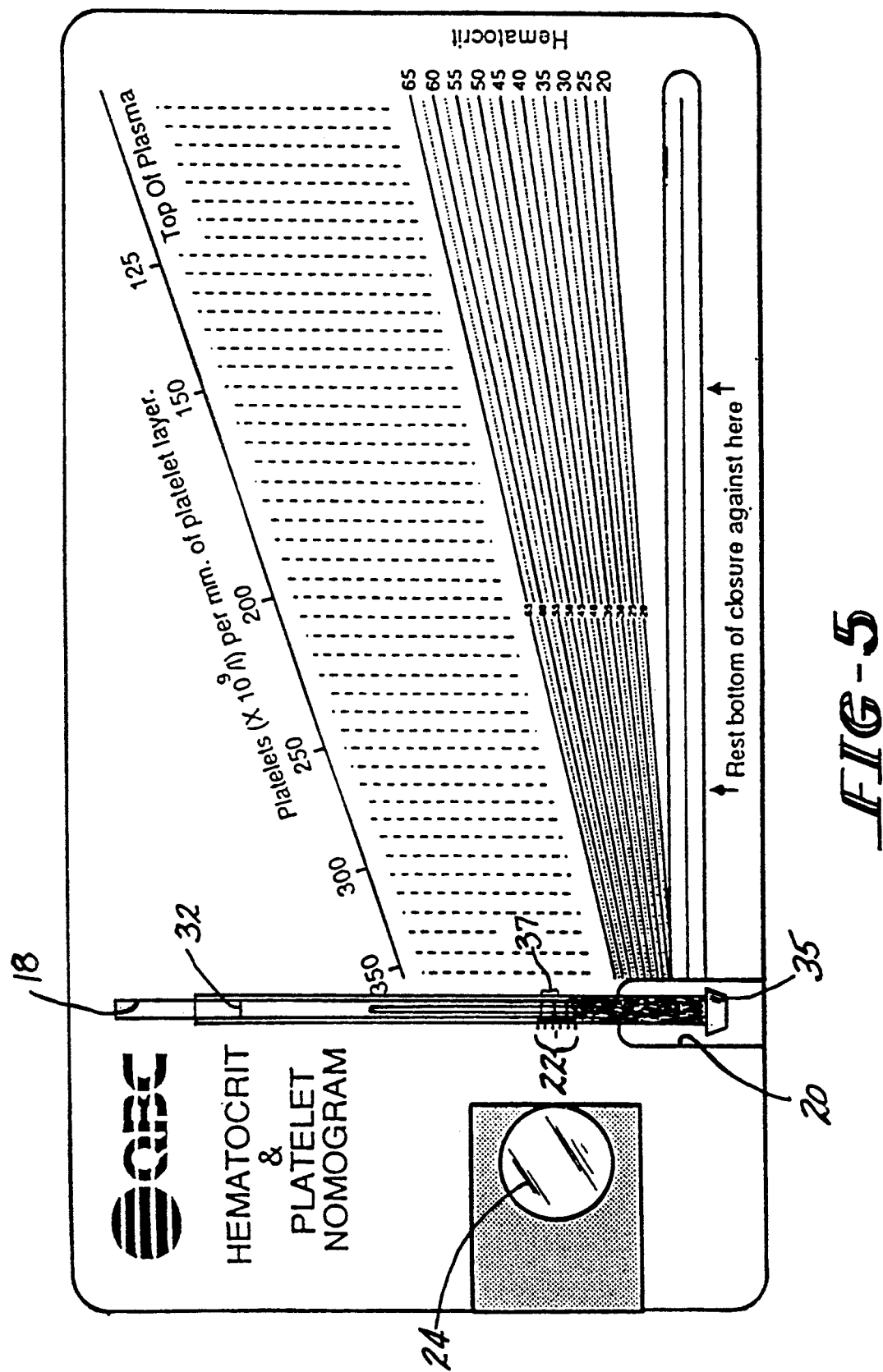
FIG. 5 is a view similar to FIG. 1 but showing the tube in position on the device for measuring the length of the particular buffy coat constituent layer.

FIGS. 4–6 illustrate the manner of use of the device 2. The centrifuge tube 32 is placed on the plaque and positioned thereon so that the sample top fill miniscus 34 overlies the total fill reference line 12. The bottom surface of the tube closure plug 35 is seated against the stop surface 8 and the tube 32 is properly positioned on the plaque by engagement with one of the corrugations 14. The proper platelet/mm of platelet band count is determined from the numerals on the reference line 12, and the hematocrit reading is determined from the alignment of the top miniscus 36 of the red cell layer with one of the hematocrit value reference lines in the portion 16 of the nomogram 10. The foregoing is illustrated in FIG. 4. The tube 32 is then placed in the slot 18, with the bottom closure plug 35 being disposed in the notch 20, as shown in FIG. 5. The platelet band 37, distinguishable by its differential light scattering and/or color resulting from the stain added to the blood sample, is then placed in register with the scale 22 and the length of the band 37 is measured on the scale 22 through the lens 24, as shown in FIG. 6. The platelet packing density information derived from the line 12, and the platelet band length are then converted to the platelet count with the conversion table on the back of the plaque.

It has been determined that medical personnel in the field desire to know both the hematocrit and the platelet count, if possible, when they are testing patients for the presence or absence of malaria. The nomogram is intended to provide a simple, inexpensive method of measuring hematocrits and platelet counts in centrifuged blood samples of varying volumes. It is based upon the assumption that the packed red cell layer for a given hematocrit will occupy a volume that varies linearly with the fill height of the capillary blood tube. This allows for the construction of isohematocrit lines. A technician needs only to align the top meniscus (air-plasma) of a centrifuged blood sample with the nomogram fill-line and determine the correct hemocrit from the easily visible float-packed cell interface. Moreover, each fill height is labeled with a corresponding platelets/mm of expanded platelet layer conversion factory that may be used to determine the sample's platelet count.

The nomogram was constructed in the following manner. Two sets of blood samples were used, one from patients with hematocrits in the normal range (34.4–44.8) and one constructed by dilution of whole blood with plasma. For the latter, a sample with hematocrit 40 was diluted to obtain hematocrits from 15.7 to 29.4. For each sample, blood was drawn into two capillary tubes-one at a high and one at a low volume. The fill height was measured before the addition of the float in order to make a precise calculation of total volume (conversion factor-2.222 $\mu$l/mm). The float was added and the tubes were centrifuged for five minutes. Microhematocrit tubes were also centrifuged and the lengths of the packed red blood cells and total heights were read to obtain the most accurate hematocrit values. After centrifugation, each capillary tube was placed in the prior art microprocessor instrument and the height of the packed red cell layer measured in tics. A conversion factor of 0.0127 mm/tic was used to convert these values to mm.

The total sample height in each tube was measured in millimeters and multiplied by 3.0 to become the horizontal scale of the nomogram. These values provided two points for each isohematocrit line (one at low total volume, one at high total volume).

The slope and x-intercept for each line were calculated. Hematocrits were then plotted versus slopes and versus x-intercepts. Regression lines were drawn for each graph and their equations calculated as follows:

The slopes of the isohematocrit lines varied with the hematocrit according to Hct=293.2 slope+0.45. The x-intercepts decreased according to Hct=−3.2 (x)+288.8. The equations for lines corresponding to hematocrits of 20; 25; to 65 were calculated from the above transfer functions and plotted to construct the nomogram.

Although the capillary blood tubes used above were stoppered with clay, plastic caps may also be used. These require the bottom of the cap to be dropped 2.4 mm from the zero hematocrit line (red cell-clay interface). This corrects for the 1.9 mm distance between the bottom of the cap and the blood/plastic interface, and also for the 0.5 mm increase in sample height due to the plastic projection at the base of the cap.

Figure 7:
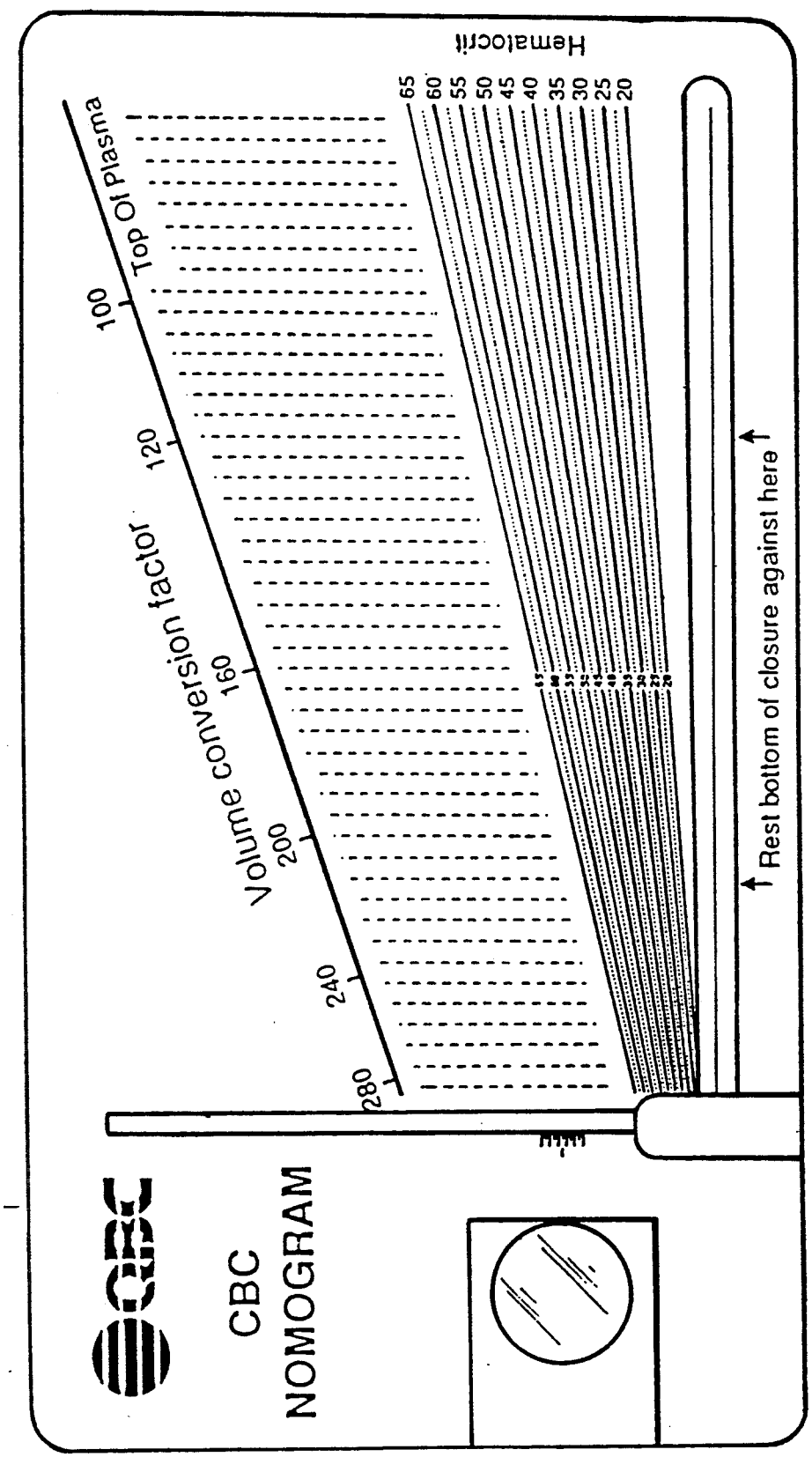
FIG. 7 is a view similar to FIG. 1 but showing an embodiment of the invention configured to measure constituent white cell component counts.

FIGS. 7 and 8 disclose an embodiment of the device which is adapted to derive differential white cell counts.

It will be readily appreciated that the device of this invention can be used to quickly derive blood constituent information from a centrifuged sample of blood in a transparent tube. The device can be used in ambient light and in the field without the need of involving microprocessor operated instruments. While use of the device has been specifically described in connection with determining blood counts, the device can also be used to determine constituent counts for other multi-constituent biological fluids, such as semen.

Since many changes and variations of the disclosed embodiment of the invention may be made without departing from the inventive concept, it is not intended to limit the invention otherwise than as required by the appended claims.

What is claimed is:

1. A device for use in measuring blood cell constituent counts in a sample of centrifuged blood contained in a transparent centrifuge tube having a constituent buffy coat layer-elongating float in the blood sample, said device comprising:
   a) a plaque for supporting the centrifuge tube;
   b) a stop surface formed on one surface of said plaque, said stop surface being operable to engage one end of said centrifuge tube; and
   c) mathematically derived nomogram indicia means printed on said plaque adjacent said stop surface, said nomogram indicia means including a red cell layer nomogram scale and a separate nomogram scale for measuring at least one buffy coat constituent band, said nomogram scales being operable to provide red cell and buddy coat constituent band layer readings from a sample of blood in the centrifuge tube when the latter is disposed on said plaque, said nomogram scales being adjusted to account for the presence of the float in the blood sample;
   d) conversion table means on said plaque for converting observed buffy coat constituent band layer readings into buffy coat constituent counts; and
   e) a plurality of surface corrugations on said plaque, said corrugations extending from said stop surface across said nomogram indicia means, and said corrugations providing a plurality of adjacent parallel grooves operable to properly position a centrifuge tube in a plurality of different locations along said nomogram indicia means.

2. The device of claim 1 wherein said red cell layer nomogram scale is adjusted to account for the presence of a red cell densifying reagent in the blood sample.

* * * * *